(12) United States Patent
Yan et al.

(10) Patent No.: US 6,399,812 B1
(45) Date of Patent: Jun. 4, 2002

(54) PRODUCTION OF ALIPHATIC ESTERS

(76) Inventors: Tsoung Y. Yan, 2427 Fairmount Ave., Philadelphia, PA (US) 19130; Jen-Ray Chang, No. 549 Shin-Sheng Rd., Chia-Yi (TW)

( * ) Notice: Subject to any disclaimer, the term of this patent is extended or adjusted under 35 U.S.C. 154(b) by 0 days.

(21) Appl. No.: 09/559,339

(22) Filed: Apr. 27, 2000

(51) Int. Cl.[7] .......................... C07C 69/02; C07C 67/48
(52) U.S. Cl. ...................... 560/231; 560/231; 560/248
(58) Field of Search ................................ 560/231, 248

(56) References Cited

U.S. PATENT DOCUMENTS

| | | | |
|---|---|---|---|
| 4,275,228 A | 6/1981 | Ctrceffaz et al. | 560/247 |
| 4,313,960 A | 2/1982 | Campagne | 426/17 |
| 4,720,457 A | 1/1988 | Armstrong et al. | 435/135 |
| 4,780,566 A | 10/1988 | Braca et al. | 560/265 |
| 4,795,853 A | * 1/1989 | Miller et al. | |
| 4,886,905 A | 12/1989 | Larkins, Jr. | 560/265 |
| 5,009,872 A | 4/1991 | Chuang et al. | 423/245 |
| 5,241,106 A | 8/1993 | Inoue et al. | 560/247 |
| 5,302,747 A | 4/1994 | Nelson et al. | 560/265 |
| 5,334,751 A | * 8/1994 | Lemanski et al. | |
| 5,770,761 A | 6/1998 | Lin et al. | 560/231 |

FOREIGN PATENT DOCUMENTS

BR 9105300 * 8/1992

OTHER PUBLICATIONS

I&EC Research vol. 38, No. 4 pp. 1271–1276, 1999, Tzong-Bin Lin, Dong–Lin Chung, and Jen–Ray Chang.

* cited by examiner

Primary Examiner—Gary Geist
Assistant Examiner—Farhad Forohar

(57) ABSTRACT

Aliphatic esters, R'COOR are produced by reacting the corresponding alcohol, ROH having carbon numbers of the alkyl groups, R' and R, between 0 and 9 and 1 and 10, respectively, with molecular oxygen in the presence of a dual functional catalyst comprising metal on acidic solid support. In particular, the process is used advantageously for production of ethyl acetate by conversion of ethanol. The reaction mixture from the reactor is separated through azeotropic distillation to recover the ethyl acetate as product and the by-product, acetaldehyde and acetic acid which could be recycled for further reaction. The process is characterized by high conversion of ethanol, high selectivity and high yield for ethyl acetate and low waste stream generation. The preferred catalyst is Pd on zeolites which is active, selective, stable and regenerable.

16 Claims, 1 Drawing Sheet

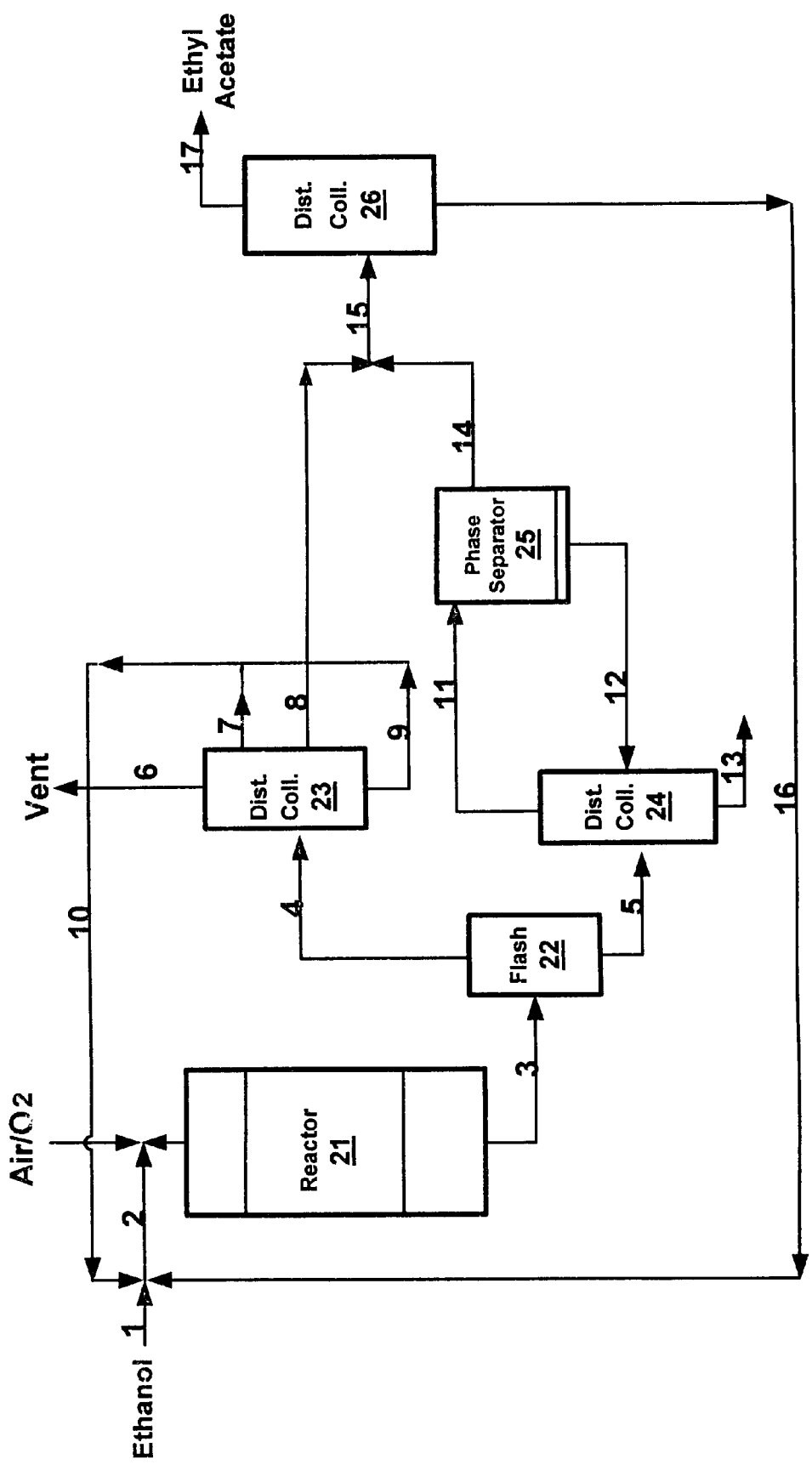
Figure

PRODUCTION OF ALIPHATIC ESTERS

CROSS-REFERENCE TO RELATED APPLICATION

Not applicable.

BACKGROUND

1. Field of Invention

This invention relates to a process for production of aliphatic esters by catalytic conversion of the corresponding alcohols having carbon numbers between 1 and 10. In particular, the process can be used advantageously for production of ethyl acetate by conversion of ethyl alcohol.

2. Description of Prior Art

Ethyl acetate is a commercially important chemical. It is especially suitable as a solvent for extraction processes in the food industry. It finds applications as a high-grade defatting detergent. It is used for preparation of cosmetics, glues, lacquers, paint as well as polymer solution in paper industry. High purity ethyl acetate is used as an anhydrous medium and also as an intermediate in chemical syntheses.

Commercially, ethyl acetate is recovered as a by-product or produced through chemical synthesis. In 1988, 65 and 35% of ethyl acetate produced in the US were from by-product recovery and chemical synthesis, respectively.

Ethyl acetate is recovered as a by-product from n-butane liquid phase oxidation and as a co-product in polyvinyl butyral production process.

As the demand for ethyl acetate increases due to environmental concerns, more ethyl acetate has to be produced through chemical syntheses. Currently, there are two commercial processes for synthesizing ethyl acetate, namely, the Hoechst process based on the Tischenko reaction and the esterification process based on direct reaction of acetic acid with ethanol. In the Tischenko reaction, acetaldehyde is dimerized to ethyl acetate in the presence of aluminum ethoxide. In the direct esterification process, ethanol is reacted with acetic acid in the presence of acidic catalyst.

In the Hoechst process, a catalyst solution of aluminum ethoxide is first prepared by dissolving granular aluminum in an ethanol-ethyl acetate mixture in the presence of aluminum chloride and a small amount of zinc chloride. The reaction evolves hydrogen and is exothermic. Intensive cooling is required to prevent the loss of organic matter. The final solution contains about 2% aluminum. The next step in the process is to introduce the catalyst solution along with acetaldehyde simultaneously into a reactor. The reaction varies according to the temperature and the catalyst quantity. These parameters are adjusted to accomplish about 98% conversion in one pass through the reactor. A further 1.5% transformation is obtained in the stirring vessels where a residue is separated from the product. The reactor is kept cooled to about 0° C. by the use of a chilled brine. The residence time in the reactor is about one hour. The distillable products are removed in the residue separation vessel by evaporation. The residue is treated with water to convert as much as possible to ethanol. The remainder can either be treated in a biological degradation plant or incinerated. The combined distillable products are then separated in a series of distillation steps to give ethyl acetate, the product; unconverted acetaldehyde for recycle: light ends which can be used for fuel; a mixture of ethyl acetate and ethanol, which can be used in the catalyst preparation step; and a by-product, acetaldehyde diethyl acetal, which can be recovered for sale or hydrolyzed for recovery of acetaldehyde and ethanol. This process is complicated in operation procedures and equipment in the processing steps. It employs expensive and dangerous catalyst systems.

In the esterification process, ethanol and acetic acid are combined with a recycle of crude ethyl acetate in a reactor, which is also an azeotropic distillation column. The reaction produces water as a waste product. The water impedes the reaction, and the reaction column removes the water as an azeotrope as it is generated. The overhead condensate is collected in a decanter where the product separates into two phases. The organic phase is partially recycled to the reaction column and the balance is fed to a second distillation column, which produces a bottom product of ethyl acetate and an overhead product of an azeotrope of ethyl acetate, water and ethanol. The overhead condensate is collected in a second decanter, where it separates into two phases as before. The organic phase is recycled to the column while the aqueous phase is combined with the aqueous phase from the first column and fed to a third column to produce a waste stream from the bottom and the azeotrope from the top. The azeotrope is recycled to the reaction column. Since esterification is a reversible reaction, the conversion per pass is theoretically limited by the equilibrium constant K which is defined as follows: $K=[ETOAC]\times[H_2O]/[ETOH]\times[HOAC]$, where [ETOAC], [H$_2$O], [ETOH] and [HOAC] are mole % of ethyl acetate, water, ethanol and acetic acid in the reactor, respectively. In order to overcome this problem, several azeotropic distillation columns with recycle as well as catalytic distillation can be used, leading to complicated and expensive operation. Furthermore, water in the ethanol feed impedes the reaction and limits conversion level of the esterification so that an expensive ethanol of low water content has to be used.

Ethyl acetate is synthesized from ethylene and acetic acid. U.S. Pat. No. 4,275,228 disclosed that ethyl acetate is prepared by vapor phase reaction of ethylene and acetic acid in the presence of a catalytic amount of a solid, ion-exchange fluoropolymer comprising sulfonic acid moieties. Conversions of acetic acid vary from 30% at 126° C. with a residence time of 55 hours to 60% at 150° C. with a residence time of 30 hours. Obviously, the reaction rate is too low to be commercially viable. In addition, the ion-exchange resin catalyst in the high temperature, oxidative reaction condition would itself be oxidized leading to rapid aging and crumbling. For the similar process, U.S. Pat. No. 5,241,106 reveals a variation whereby the catalyst comprises tungstophosphoric acid of which 10–90% of the total amount of proton is replaced with a member selected from the group consisting of (a) cesium metal ion, (b) a combination of cesium metal cation and at least one cation selected from alkali metal cations other than cesium cation, and (c) a combination of cesium metal cation and at least one cation of iron group metal cations. The process is flexible and can be carried out in either vapor or liquid phase. In addition, the reaction rate can be improved by adding control amount of water in the feed. However, the reaction rate and the yield of ethyl acetate remain too low for commercial application.

Ethyl acetate is produced by hydrogenation of acetic anhydride. U.S. Pat. No. 4,886,905 disclosed a process for preparation of ethylene diacetate and/or ethyl acetate by hydrogenating acetic anhydride in the presence of a homogeneous ruthenium catalyst, methyl iodide and, optionally, lithium iodide. The process can also be utilized to hydrogenate mixtures of acetic anhydride and ethylene diacetate to produce ethyl acetate alone. This process is complex to operate. It requires the use of homogeneous complex catalyst. The co-product, acetic acid, must be separated and converted back to acetic anhydride for reuse. In addition, the catalyst and iodides must be separated from the reaction products and recycled.

Another approach is to produce ethyl acetate from methyl acetate. In U.S. Pat. No. 4,780,566, a process is described for producing ethyl acetate either alone or in mixture with acetic acid, by homologation of methyl acetate with CO and $H_2$ in the presence of a catalyst in the form of a Ru compound and catalysis promoter of hard acid type in an atmosphere of hydrogen and carbon dioxide. This process is not only complex but also poor in selectivity for ethyl acetate. It produces significant amount of by-product, acetic acid, alcohols, ethers, propionates, methane and ethane.

Ethyl acetate is produced by catalytic oxidation of ethanol. U.S. Pat. No. 5,334,751 disclosed a process for making ethyl acetate which comprises reacting in a reaction zone ethanol and molecular oxygen in the presence a solid catalyst containing the elements and protons indicated by the empirical formula, Pd(a)M(b)TiP(c)O(x) where M is selected from Cd, Au, Zn, Tl, alkaline earth metals. In addition, the catalyst contains crystalline TiP(2)O(7). The process is simple but might be difficult to avoid temperature run-away. In addition, the reaction temperature is so high that significant by-product is produced and purification of the product becomes difficult. The selectivity for ethyl acetate is poor and co-produces up to 75.5% of acetic acid, which has to be separated and sold. Further more, the presence of high level of acetic acid and water in the system causes corrosion of equipment and, particularly destruction of the catalyst.

In U.S. Pat. No. 5,770,761, a process is disclosed for oxidation of liquid ethanol in the presence of excess liquid ethanol and supported oxidation catalyst to produce ethyl acetate in one step. In the process, two chemical reactions are involved and two catalysts are used. For oxidation portion of the process, metallic oxidation catalyst on a hydrophobic support is preferred. For the esterification portion of the process, an acidic solid ion exchange resin is preferred. In the process, the selectivity for ethyl acetate is low so that the yields of ethyl acetate was between 10 and 40% and mostly around 20%, while the by product, acetic acid is around 10%. The low selectivity and yield of ethyl acetate makes the process inefficient and costly. As in a typical oxidation process, a significant amount of unknown by-product is co-produced in the process to complicate the product purification operation. The types and the amount of by-product increase greatly as the temperature is increased to increase the conversion levels of ethanol. It makes production of valuable, high purity ethyl acetate difficult and costly. The by-products also destroy the catalyst. As Lin et al. showed in the article published in I&EC Research Vol.38, No.4, page 1271–1276, 1999 that significant amount of by-products in the system, particularly, acetic acid causes loss of the Pd metal through a leaching process. They also cause migration of Pd leading to loss in catalyst activity and selectivity for ethyl acetate. The resins used as the oxidation catalyst support and acidic ion exchange catalyst disintegrate in the oxidative environment of the process. In the reaction system, said resins are oxidized itself leading to aging and crumbling. Thus further improvement is required to make the process technically and economically viable.

The prior art for production of aliphatic esters, particularly, ethyl acetate suffers from a number of disadvantages including:

a. Ethanol conversion levels are low leading to low yield of ethyl acetate. When severity of the process is increased by, for example, increasing temperature to increase the conversion of ethanol, copious amount of $CO_2$ will be produced due to over oxidation.

b. Its selectivity for ethyl acetate is low and it co-produces significant amount of acetic acid. In a liquid phase operation, co-production of acetic acid in a significant amount is inevitable because the esterification step is limited by thermodynamic equilibrium. The presence of high level of acetic acid lead to corrosion of the equipment and damage to the catalyst.

c. The resins used as the oxidation catalyst support and acidic ion-exchange resin catalysts are destroyed in the oxidative reaction environment. The resins are oxidized themselves leading to aging and crumbling. The oxidation and destruction of the resin is further accelerated when it is loaded with metal component for use as an oxidation catalyst. Thus, the resin-based catalyst cannot be used in oxidation process for extended period of operation time, d. In the liquid phase operation, the by-product, acetic acid damages the catalyst. It leaches out the metal such as Pd leading to loss of catalyst activity. The presence of acid also causes agglomeration of metals such as Pd on the support to deactivate the catalyst.

e. The by-product, acetic acid not only lowers conversion of ethanol per pass but also requires complicated system for separation and extensive recycling.

f. The non-selective oxidation involved in the process produces excess amount of $CO_2$ causing loss of raw material, and significant amount of impurities causing difficulties in purification of ethyl acetate product.

g. The reaction conditions of the process are severe in order to increase the conversion level of ethanol. Thus, high temperature and pressure conditions are employed.

h. The significant amount of by-products from the oxidation process such as acetaldehyde and acetic acid have to be disposed or recovered for sale. This need causes environmental concerns and complicates the production of ethyl acetate.

There is a need in the industry for a more efficient and earth friendly process for the production of ethyl acetate.

The disclosures of the above patents and literature are incorporated herein by reference.

SUMMARY OF THE INVENTION

The present invention provides a process for production of aliphatic esters, R'COOR by reacting the corresponding alcohol, ROH with molecular oxygen in the presence of a dual functional catalyst comprising metal on acidic support. The carbon numbers of the alkyl chains, R' and R are 0 to 9 and 1 to 10, respectively. In particular, the process is employed advantageously to produce ethyl acetate by conversion of ethanol. The reaction mixture from the reactor is separated through azeotropic distillations in three columns to recover ethyl acetate product and by-product, acetaldehyde and acetic acid for recycle. The preferred catalyst is Pd on acidic Zeolite Y. It is active for ethanol conversion, selective for ethyl acetate and can regenerated by air oxidation. The reaction can be operated in either vapor or liquid phase but vapor phase operation is preferred for production of ethyl acetate. The process is characterized by high conversion of ethanol, high selectivity for ethyl acetate, low waste generation and stable operation.

Objects and Advantages

Accordingly, several objects and advantages of the present invention are:

a. To provide a process for conversion of an alcohol, ROH to an aliphatic ester, R'COOR, particularly, ethanol to ethyl acetate at high conversion levels and high yield of the ester, particularly, ethyl acetate.
b. To provide a process for production of ethyl acetate from ethanol with high selectivity for ethyl acetate and low selectivity for acetic acid.
c. To provide a dual functional catalyst which is stable in the oxidative reaction environment.
d. To provide a dual functional catalyst which is stable in activity and integrity at the reaction environment of present invention for extended period of operation time.
e. To provide a process which breaks the thermodynamic equilibrium limitation to minimize production of acetic acid.
f. To provide a process for converting an alcohol to ester which minimizes production of $CO_2$ and impurities.
g. To provide a mild process for ester production at low pressure and low temperature.
h. To provide an earth friendly process for ester production which minimizes waste generation.

Further objectives and advantages will become apparent from a consideration of the ensuing description and drawing.

BRIEF DISCRIPTION OF THE DRAWING

The embodiment of the invention illustrated in the schematic drawing shows a conversion reactor and the various distillation columns, which are interconnected to produce ethyl acetate of high purity.

DESCRIPTION OF THE INVENTION

To simplify the description and discussion, ethyl acetate is used to represent the aliphatic ester, R'COOR. In accordance with this invention, high quality ethyl acetate is produced by reacting ethanol with oxygen through complex reactions. It is believed that the major reaction takes place in at least two steps. In the first step, ethanol is oxidized by oxygen to acetic acid and water. This oxidation step is catalyzed by metals, such as Pt, Pd as well as group VIII metals. It is this reaction step that non-selective oxidation takes place to form excessive amount of $CO_2$ and other impurities. It has been found that proper choice of metal and operating mode will minimize these non-selective reactions. In the second step of the reaction, ethanol is reacted with acetic acid to form ethyl acetate through esterification. The completeness of esterification is governed by thermodynamic equilibrium constant. The thermodynamic equilibrium constant, K is equal to the product: $[ETOAC] \times [H_2O]/[ETOH] \times [HOAC]$ where $[ETOAC], [H_2O], [ETOH]$, and $[HOAC]$ are concentration (mole %) of ethyl acetate, water, ethanol and acetic acid in equilibrium reaction mixture. The equilibrium constant between 50 and 150° C. is about 3.7. Since water is formed in the first step of the reaction and carried in with feed, the conversion cannot be pushed over the equilibrium limit in the prior art process. As will be discussed later, this limitation is overcome in the preferred embodiment of present invention.

Accordingly, the critical factors in the process of this invention are three, namely, active, selective and stable catalyst, noble process configuration and the proper operating conditions.

Catalysts

In the present invention of converting ethanol with oxygen to ethyl acetate, the catalyst is critically important. As discussed above, the process for converting ethanol requires two types of catalysts, one for oxidation of ethanol and the other for esterification of acetic acid with ethanol. U.S. Pat. No. 5,770,761 teaches use of metallic catalyst on a hydrophobic support for the oxidation step and an acidic ion-exchange resin for the esterification. These two separate catalysts are placed in separate reactors in series or mixed together and placed in a reactor. In either case, two separate catalysts are employed leading to higher catalyst cost. In addition, in the two reactors system, the acetic acid content in the first reactor is high so as to cause serious leaching of the metal catalyst and corrosion of the equipment. In the single reactor with mixed catalyst, it is a challenge to load the catalyst uniformly and keep it from segregation during the operation. Furthermore, recovery of the spent catalysts become complicated. Now, it has been discovered that a novel catalyst with the two required catalytic functions, which is particularly effective in catalyzing the reactions of present invention can be prepared. This dual functional catalyst is comprised of a metal for the oxidation step and an acidic support for the esterification step. Here, the acidic support serves two functions, namely, acidic catalyst and the support for the metallic oxidation catalyst. Thus, suitable catalysts include metals on a catalytically active acid support as heterogeneous catalysts.

In the present invention, useful heterogeneous catalysts may contain metals from Group IB, IIB, IVB, VIB, VIIB or VIII of the Periodic Table of the Elements, published by Sargent-Welch of Skokie, Ill. Within the group, Ni, Mo, W, Co, Pt. Pd, Rh, Ru, Ag, Au, Zn, Cu and Cr are preferred. Pt and Pd are most preferred metals. Combinations of noble metals such as platinum-rhenium, platinum-palladium, platinum-iridium or platinum-iridium-rhenium together with combination with non-noble metals, particularly of Groups VIB and VIII are of interest, particularly with metals such as Co, Ni, V, W, and Mo, for example, platinum-tungsten, platinum-nickel or platinum-nickel-tungsten, palladium-tungsten, palladium-nickel, or palladium-nickel-tungsten. The metal can be used in the forms of reduced metal, oxide and sulfide.

U.S. Pat. No. 5,770,761 teaches use of hydrophobic support such as styrene-divinylbenzene copolymer (SDB). SDB is an inert support and catalyzes neither oxidation nor esterification. However, in the present invention, catalytically active acidic supports is employed with examples including one or more of silica-alumina, zeolites, clays, Kieselguhr, titania, magnesia, and active carbons from sources such as coal, coke, and coconut shell. Beside the acidity requirement, the support should be stable at the oxidative and high temperature reaction conditions involved in the present invention. For example, both organic resins and ion exchange resins taught in the U.S. Pat. No. 5,770,671 are not suitable because they are labile to oxidation and thermal decomposition in the environment of present invention.

Suitable zeolites for use as the acidic support in the present invention include those commonly referred to as large pore, i.e., those zeolites having a Constraint Index of less than about 1, such as Zeolite X and Zeolite Y as well as those commonly referred to as medium pore, i.e., those zeolites having a Constraint Index of from about 1 to about 12. Examples of suitable medium-pore zeolites include ZSM-5, ZSM-11, ZSM-12, ZSM-22, ZSM-23, ZSM-35, ZSM-48 and Modernite. Zeolite beta, known to exhibit characteristics of either a large pore zeolite or a medium-pore, is also useful in the present invention. It has been found that zeolites of high silica-alumina ratio are more stable under the oxidative-hydro-thermal conditions encountered in the present invention. For example, Y or ultra-stable Y with silica-aluminum ratio greater than 5 are preferred over regular Zeolite Y. U.S. Pat. No. 5,009,872 teaches a method to render silica granules hydrophobic by treatment with methylsilane. This is an expensive process in catalyst preparation. It has been discovered that the acidic support used in the present invention requires no such treatment to render it hydrophobic.

In preparation of the dual functional catalyst useful in the present invention, metals may be added to the supports by impregnation, mulling, mixing, coprecipitation or a combination of one or more of these techniques. For zeolites, the metals can be incorporated advantageously by ion exchange. The amount of metal loading on the support is suitably from 0.01 to 20% by weight, normally 0.1 to 10% by weight, although this will, of course, vary with the nature of the metal component, less of the highly active noble metals, particularly, platinum and palladium, being required than of the less active metals. It has been discovered that the activities of metal and acid support must be balanced to achieve the best result. The approaches to achieve this balance include varying the activities of the metal and acidic support components and the metal loading.

The catalyst prepared by loading metals on the support as described above is dried and calcined in air up to 500° C. for several hours. The finished catalyst is in an oxide form and can be used directly. However, the catalyst in oxide form can be reduced or sulfided before use.

Process Configuration

A preferred embodiment of the present invention is shown in the Figure. In accordance with the drawing, an ethanol feed from line 1 is mixed with acetaldehyde by-product and part of unconverted ethanol from line 10 and the rest of unconverted ethanol from line 16. The mixture is mixed with air or oxygen in line 2 and introduced into reactor 21. It has been discovered that, in addition to anhydrous ethanol, commercial and lower grade ethanol can be used as the feed. As a result, a bottom from distillation column 26, which contains unconverted ethanol and small quantity of water can be directly recycled from line 16. Reactor 21 is a fixed bed filled with a dual functional catalyst comprising metal on acidic support according to the present invention. The feed mixtures are reacted in reactor 21 at temperatures between about 40 and 200° C. and pressures between 0 and 1000 psig. In the reactor, ethanol reacts with oxygen in the presence of the dual functional catalyst to form ethyl acetate, water, acetic acid and small quantity of the by-product, acetaldehyde, which can be recycled for further reaction to yield the desired product, ethyl acetate. It is surprising that the yields of these by-products are so small in comparison with those in the prior art. It has been discovered that the yields of these by-products can be reduced further by choosing proper operating conditions.

Depending on the combination of temperature and pressure as well as the nature of the oxygen supply, the reaction can take place in either liquid or vapor phase. For example, in conversion of ethanol with air at 15 psig, the reaction becomes substantially vapor phase when the reaction temperature is about 70° C. or higher. It has been discovered that, in comparison with the liquid phase operation, the conversion is higher, the selectivity is better and the catalyst is more stable in the vapor phase reaction. It is believed that in the vapor phase operation, the thermodynamic limitation in the degree of esterification is overcome. Esterification is catalyzed by the acidic component of the catalyst and takes place mainly on the catalyst surface. Thus, thermodynamic equilibrium among the reaction mixture can be reached on the catalyst surface. However, because of the poor relative affinity of ethyl acetate relative to other polar compounds, mainly water, ethanol and acetic acid, ethyl acetate leaves the reacting catalyst surface and jumps into the vapor phase as it is formed. Since the ethyl acetate is continuously removed from the reacting surface, the thermodynamic equilibrium limitation is overcome. Without the presence of catalyst, little esterification takes place in the vapor phase. Thus, the ethyl acetate escaped into the vapor phase can exit the reactor at high concentrations without thermodynamic limitation. In short, the reactor operated in the vapor phase serves as a catalytic distillation unit as well. Thus, even though the present invention is workable in both liquid and vapor phases, vapor phase operation is preferred. The use of vapor phase operation is in direct contrast to use of liquid phase operation taught in U.S. Pat. No. 5,770,761.

The reaction mixture from reactor 21 is charged into flash separator 22 via line 3. The vapor phase from 22 is charged to distillation column 23 through line 4. In column 23, the mixture is separated into acetaldehyde, which is recycled for further reaction through line 7, ethanol, which is recycled for reaction through line 9 and the crude product, ethyl acetate is charged to distillation column 26 via line 8. The non-condensable gas is flared or used as fuel through line 6. The liquid phase from separator 22 is charged to distillation column 24 through line 5. From column 24, the overhead is introduced to phase separator 25. The top phase from separator 25 is crude ethyl acetate and charged to distillation column 26 through line 15 upon mixing with the crude ethyl acetate from line 8 for purification to obtain high purity ethyl acetate product. The water rich bottom phase from separator 25 is returned to column 24 through line 12 for further rectification. The bottom from distillation column 24 is water with trace of acetic acid and discharged through line 13 for waste disposal or acetic acid recovery for further reaction. Three distillation columns are required to recover high purity ethyl acetate because of azeotropic formation.

Process Conditions

According to the present invention, ethanol feed is reacted with oxygen in the presence of a dual functional catalyst in at least two steps to form ethyl acetate.

In theory, anhydrous ethanol of 99%+ purity is most ideal for this reaction. However, it has been discovered that through improvements in process configuration and operation in vapor phase, commercial grade ethanol of about 92% purity and other available ethanol with purity substantially lower than 95% can be advantageously employed to save the feed cost. In addition, the small quantities of by-products, acetaldehyde and acetic acid can be recycled for further conversion to ethyl acetate to minimize waste disposal.

Stoichiometrically, the feed ratio of ethanol to oxygen for the reaction is 1 by mole. However the reaction works well where the ratio is in the range of about 0.4 to 5 and preferably 0.6 to 3. As the source of oxygen, either pure oxygen or air can be employed.

The reaction temperature should be high enough to obtain the desired level of ethanol conversion but low enough to obtain good selectivity for ethyl acetate and minimize the yields of by-products. The reaction temperature will generally be in the range of 40 to 250° C. and preferably 50 to 150° C. With a more active catalyst, lower temperatures within the range should be employed to minimize over reaction. The reaction pressure will usually be in the range of about 0 to 1500 psig, and more commonly in the range of 1 to 1000 psig. A combination of reaction temperature and pressure is the major factor in determining the phase of the reaction mixture in the reactor. For example, at a reaction pressure of 15 psig, the reaction becomes substantially vapor phase when the reaction temperature is about 70° C. or higher. It has been discovered that the reaction in the present invention can be carried out advantageously in vapor phase. In the vapor phase operation, the thermodynamic limitation on conversion to ethyl acetate is overcome leading to high conversion of ethanol, high yield and high purity of ethyl acetate. In addition, metal leaching from the dual functional catalyst is essentially eliminated in the vapor phase operation. Furthermore, the reaction mixture in the vapor phase is substantially less corrosive to equipment than that in the liquid phase operation.

Space velocities are normally held in the range of about 0.1 to 10, preferably about 0.3 to 5 of weight hourly space velocity (WHSV). At a reaction temperature, the conversion level of ethanol increases as the space velocity is reduced. Thus, by lowering the space velocity, the reaction temperature can be lowered to get high selectivity for ethyl acetate and minimize the by-products yield while the conversion level is maintained.

The conversion level of ethanol is normally maintained in the range of about 5 to 99%, preferably about 10 to 95% by adjusting the reaction temperature, pressure and space velocity. To facilitate recovery of ethyl acetate as the product and ethanol and acetic acid for recycle, ethanol conversion of substantially greater than about 20%, preferably about 30% is maintained at low reaction temperatures.

The invention is illustrated by the following examples in which all parts, proportions and percentages are by weight unless the contrary is stated.

Experiments

Laboratory experiments were carried out to demonstrate the viability of the present invention.

Catalysts and its preparation:

Pd on Zeolite Y is a dual functional catalyst of the present invention. It was prepared from Zeolite Y with silica-aluminum ratio of 56 and surface area of 800 m$^2$/g from TOSOH of Japan. To the water slurry of said Zeolite Y, added predetermined amount of Pd(NH$_3$)$_4$(NO 3)$_2$, evacuated under vacuum at room temperature for 8 hours to remove the excess water and finally calcined in flowing air to 400° C. for 8 hours.

Pd on SDB was prepared according to the teaching of U.S. Pat. No. 5,770,761. The styrene divinylbenzene (SDB) co-polymer was prepared by co-polymerizing styrene and divinylbenzene using 2,2-azobis(2-methylpropionitrile) as an initiator. The surface area of SDB was 465 m$^2$/g. The Pd/SDB catalyst was prepared by impregnating SDB with predetermined amount of Pd(NH$_3$)$_4$Cl$_2$. H$_2$O. The Pd content in the final Pd/SDB was 1%.

Acidic ion-exchange resin, Amberlyst 15 was obtained from Rohm and Hass, Philadelphia, Pa. It was used as a mixture with Pd/SDB as taught in U.S. Pat. No. 5,770,761. The ratio of Pd/SDB to Amberlyst 15 was 1 to 2.

Pt on ZSM-5 is also a dual functional catalyst of the present invention. It was prepared by impregnating ZSM-5 with Pt(NH$_3$)$_4$(NO$_3$)$_2$ by employing a procedure similar to that for Pd on Zeolite Y.

Apparatus:

The catalysts were tested in a flow system having a fixed bed reactor with an inside diameter of 2.1 cm and volume of 94.0 ml. The reactor was heated using a oil bath circulator to assure a steady reaction temperature. The reaction temperature was monitored and controlled using a sensor located at the center of the catalyst bed.

The reaction products were trapped using a condenser at −5° C. Both liquid and gaseous products were analyzed using a gas chromatography, Shimadzu Model GC 14-B.

Test procedure:

The reactor was packed with the catalyst to be tested and placed in a flow reaction system. Ethanol feed and air or oxygen at the desired rates was metered into the reaction system using mass flow controllers. Unless specified, the ethanol feed was a commercial grade of 92% ethanol content. Upon mixing, the mixtures flow downward through the reactor to carry out the reactions at the desired temperature and pressure. The reactor effluent was cooled and recovered for analyses. Based on the material balances of test results, performance parameters such as conversion, selectivity, purity and "composition products" were calculated. The composition product P is defined as follows: P=[ETOAC]×[H$_2$O]/[ETOH]×[HOAC] where [ETOAC], [H$_2$O], [ETOH] and[HOAC] are concentrations in mole % of ethyl acetate, water, ethanol and acetic acid in the reaction product, respectively. The composition product P is useful in determining if the reactor effluent is in thermodynamic equilibrium. When P is smaller than the thermodynamic equilibrium constant K, which is around 3.7 at the operation range of this invention, the reaction has not achieved thermodynamic equilibrium yet. On the other hand, when P is greater than K, the reaction has overcome the thermodynamic equilibrium limitation. Except composition product P, all calculations were based on dry feed to make it easier to compare the catalyst performances.

EXAMPLE 1

This example shows the performance of Pd on Zeolite Y at the preferred embodiment of present invention. The conversion of ethanol was 83.3% based on the feed as charged and 78.1% based on dry feed. The yield of ethyl acetate reached 49.6 % while acetic acid was kept at a low level of 7.5%. The composition product of this product mixture was 20.7 far exceeding the thermodynamic equilibrium constant of 3.7. Obviously, the thermodynamic limitation was overcome at the vapor phase operation in this experiment. The unidentified species only amounted to 0.4%, which makes purification of ethyl acetate easy.

TABLE 1

Performance of Pd on Zeolite Y
Catalyst: Pd on Zeolite Y
Temperature, ° C.: 110
WHSV, W/W/Hr.: 1.0
Feed: Ethanol with 8% water
Pressure, atm.: 2

| PRODUCT | COMPOSITION |
|---|---|
| ETOAC (wt %) | 49.6 |
| ETOH (wt %) | 16.7 |
| HOAC (wt %) | 7.5 |
| CH₃CHO (wt %) | 0.5 |
| H₂O (wt %) | 22.4 |
| Fuel gas (wt %) | 2.9 |
| Total unidentified Species (wt %) | 0.4 |
| Composition Product, P | 20.7 |

EXAMPLE 2

In this example, the performances of Pd on Zeolite Y of the present invention was compared with that of catalyst mixture of Pd/SDB and Amberlyst 15 as taught in the U.S. Pat. No. 5,770,761. The results are shown in Table 2. Sine the prior art teaches that operation should be in liquid phase, the reaction pressure was set at 30 atm. to assure liquid phase operation for Pd/SDB-Amberlyst 15 while the pressure was set at 2 atm. to assure vapor phase operation for Pd on Zeolite Y. At the testing temperature of 90° C., the Pd/SDB-Amberlyst 15 catalyst was too low in activity so that its liquid space velocity was decreased to 0.5 vs. 1.0 for Pd on Zeoloite Y in order to make a better comparison. The results show that, in comparison with the Pd/SDB-Amberlyst 15, Pd on Zeolite Y was more active for higher conversion, more selective for ethyl acetate and lower selectivity for acetic acid. It is particularly important to note that the unidentified impurity was only 0.1% for Pd on Zeolite Y vs. 0.7% for Pd/SDB-Amberlyst 15. The composition products for the products from Pd on Zeolite Y and Pd/SDB-Amberlyst 15 were 19.8 and 2.8, respectively. As the theory dictates, the operation of Pd/SDB-Amberlyst 15 in liquid phase is limited by thermodynamic equilibrium, while operation of Pd on Zeolite Y in the vapor, phase according to the present invention overcame the limitation. It was noted that Pd on Pd/SDB was leached out in the reaction process and Pd was detected in the reactor effluent. There was no Pd detected in the reactor effluent from Pd on Zeolite Y.

TABLE 2

Performances of Pd on Zeolite Y and Pd/SDB-Amberlyst 15

| Catalyet: | Pd on Zeolite Y | Pd/SDB-Amberlyst 15 |
|---|---|---|
| Pressure, atm. | 2.0 | 30.0 |
| Temperature, ° C.: | 90 | 90 |
| WHSV, W/W/Hr | 1.0 | 0.5 |
| ETOAC (wt %) | 29.0 | 19.4 |
| ETOH (wt %) | 51.2 | 65.2 |
| HOAC (wt %) | 3.6 | 1.6 |
| CH₃CHO (wt %) | 0.6 | 2.7 |
| H₂O (wt %) | 13.2 | 8.5 |
| Fuel gas (wt %) | 2.3 | 1.9 |
| Total unidentified Species (wt %) | 0.1 | 0.7 |
| Composition Product, P | 19.8 | 2.8 |

EXAMPLE 3

The Pd on Zeolite Y was tested for long-term stability and regenerability of the aged catalyst. The results are shown in Table 3A and 3B. The catalyst appeared stable in activity for ethanol conversion and selectivity for ethyl acetate. After 110 hours of on-stream time, the catalyst was tested aging at severe conditions and, then, returned to the normal operation at 400 hours of on-stream time. Indeed, the catalyst was aged and ethanol conversion had decreased from 78.1 to 48%. The aged catalyst was regenerated in air at 120° C. for 8 hours and re-tested at the normal operation condition. The activity of the aged catalyst was substantially recovered and the ethanol conversion was up from 48 back to 67.8%, approaching the 78.1% for the fresh catalyst. This result indicates that Pd on Zeolite Y is regenerable. As shown in Table 3A, the composition product jumped to 4.2 above 3.7 for the equilibrium constant at 70 C indicating that the reaction phase had changed substantially from liquid to vapor. At higher temperatures, the composition products were higher than the equilibrium constant. Again the novelty of vapor phase operation of the present invention is demonstrated. The selectivity for ethyl acetate was about 80% or higher. Such a high selectivity is remarkable for the oxidation process involved in the present invention.

TABLE 3A

Effects of operating conditions, stability and regenerability
Catalyst: Pd on Zeolite Y
Feed: Ethanol with 8% water
Pressure, atm: 2

| Time on Stream, H | WRSV W/W/H | Temp, ° C. | ETOAC % | ETOH % | HOAC % | CH₃CHO % | H₂O % | Gas % | P |
|---|---|---|---|---|---|---|---|---|---|
| 10 | 1 | 50 | 8.8 | 84.3 | 1.1 | 1.2 | 4.0 | 0.6 | 2.0 |
| 26 | 1 | 70 | 10.8 | 81.4 | 0.7 | 1.6 | 4.6 | 0.9 | 4.2 |
| 42 | 1 | 100 | 24.0 | 57.5 | 2.9 | 1.2 | 10.7 | 3.7 | 5.3 |
| 58 | 1 | 110 | 32.7 | 47.6 | 1.4 | 0.5 | 13.8 | 4.0 | 19.8 |
| 86 | 0.5 | 110 | 50.0 | 16.5 | 7.5 | 0.5 | 22.7 | 2.8 | 20.7 |
| 94 | 0.25 | 110 | 56.3 | 6.8 | 8.6 | 0.5 | 25.6 | 2.2 | 52.3 |
| 106 | 1.25 | 110 | 26.6 | 55.0 | 2.5 | 1.0 | 11.6 | 3.3 | 7.5 |
| 400 | 0.5 | 110 | 17.3 | 41.2 | 25.3 | 0.6 | 14.7 | 0.9 | 0.6 |
| 420 | 0.5 | 110 | 44.1 | 33.5 | 1.1 | 0.9 | 18.4 | 2.0 | 53.3 |
| 430 | 0.5 | 110 | 43.1 | 34.2 | 0.6 | 0.8 | 17.8 | 3.5 | 90.0 |
| 450 | 0.5 | 110 | 48.1 | 25.5 | 2.6 | 0.8 | 20.5 | 2.5 | 35.6 |

TABLE 3B

Performance of Pd on Zeolite Y

| Time Hr. | WHSV W/W/H | Temp. °C. | Conv. % | Selec. % ETOAC | Selec. % HOAC | Selec. % CH₃CHO | Selec. % Fuel gas |
|---|---|---|---|---|---|---|---|
| 10 | 1 | 50 | 12.3 | 78.3 | 7.4 | 10.3 | 4.0 |
| 26 | 1 | 70 | 14.8 | 79.6 | 4.0 | 11.5 | 4.9 |
| 42 | 1 | 100 | 35.9 | 79.9 | 7.0 | 4.1 | 9.0 |
| 58 | 1 | 110 | 45.5 | 87.9 | 2.8 | 1.5 | 7.8 |
| 86 | 0.5 | 110 | 78.1 | 86.1 | 9.5 | 0.8 | 3.6 |
| 94 | 0.25 | 110 | 90.3 | 86.9 | 9.7 | 0.8 | 2.6 |
| 106 | 1.25 | 110 | 38.5 | 83.5 | 5.7 | 3.2 | 7.6 |
| 400 | 0.5 | 110 | 48.0 | 46.6 | 50.0 | 1.6 | 1.8 |
| 420 | 0.5 | 110 | 58.5 | 93.4 | 1.8 | 1.8 | 3.0 |
| 430 | 0.5 | 110 | 58.9 | 91.8 | 1.0 | 1.8 | 5.4 |
| 450 | 0.5 | 110 | 67.8 | 91.3 | 3.6 | 1.6 | 3.5 |

EXAMPLE 4

In this example, the effects of reaction temperature on the process were surveyed. The results are shown in Table 4A and 4B. The results show that both ethanol conversion and ethyl acetate yield maximize at 110 C. Thus, there is an optimum operation temperature. In a simple reaction, the conversion level increases with temperature monotonically. Thus the reactions involved in the process are complex including multi step reactions and reversible reactions.

TABLE 4A

Effects of reaction temperature on the catalyst performance
Catalyst: Pd/Zeolite Y    Feed: Ethanol with 8% water
Pressure, atm.: 30    WHSV, W/W/Hr: 1.0

| Temp, °C. | ETOAC wt % | ETOH wt % | HOAC wt % | CH₃CHO wt % | H₂O wt % | Gas wt % |
|---|---|---|---|---|---|---|
| 70 | 23.7 | 58.9 | 4.1 | 0.7 | 10.9 | 1.7 |
| 90 | 29.3 | 51.0 | 3.6 | 0.6 | 13.1 | 2.4 |
| 110 | 31.6 | 46.7 | 4.0 | 0.1 | 14.1 | 3.5 |
| 130 | 26.9 | 50.5 | 4.9 | 0.2 | 12.5 | 5.1 |
| 150 | 22.5 | 55.5 | 4.9 | 0.6 | 10.6 | 5.9 |

TABLE 4B

Effects of reaction temperature on catalyst performance

| Temp. °C. | Conv. % | Selec. % ETOAC | Selec. % HOAC | Selec. % CH₃CHO | Selec. % Fuel gas |
|---|---|---|---|---|---|
| 70 | 33.7 | 82.9 | 10.4 | 2.4 | 4.3 |
| 90 | 41.6 | 85.5 | 7.6 | 1.8 | 5.1 |
| 110 | 45.9 | 84.9 | 7.8 | 0.4 | 6.9 |
| 130 | 42.2 | 78.0 | 10.4 | 0.8 | 10.8 |
| 150 | 37.5 | 72.7 | 11.5 | 1.90 | 13.9 |

EXAMPLE 5

In this example, Pt on ZSM-5 was tested for oxidation of ethanol with air to ethyl acetate. Because of high flow rate or WHSV employed in this test, the conversion level was not high but ethyl acetate was produced with good selectivity.

TABLE 5

Performance of Pt on ZSM-5
Catalyst: Pt on ZSM-5
Temperature, °C.: 110
WHSV, W/W/Hr.: 3.0
Feed: Ethanol with 8% water
Pressure, atm.: 2

| PRODUCT | COMPOSITION |
|---|---|
| ETOAC (wt %) | 10.2 |
| ETOH (wt %) | 59.2 |
| HOAC (wt %) | 3.9 |
| CH₃CHO (wt %) | 7.4 |
| H₂O (wt %) | 14.3 |
| Fuel gas (wt %) | 4.6 |
| Total unidentified Species (wt %) | 0.4 |

EXAMPLE 6

In this example, n-propyl alcohol was reacted with oxygen over Pd on Zeolite Y catalyst. N-propyl propionate was obtained in good yield and with high selectivity. Apparently, n-propyl alcohol reacts with oxygen in a way similar to ethanol to yield the corresponding ester, namely, n-propyl propionate.

TABLE 6 n-propyl alcohol conversion catalyzed by Pd on zeolite Y
Catalyst: Pd on Zeolite Y
Temperature, °C.: 110
WHSV, W/W/Hr.: 0.5
Feed: n-propyl alcohol
Pressure, atm.: 2

| PRODUCT | COMPOSITION |
|---|---|
| n-propyl propionate (wt %) | 44.1 |
| n-propyl alcohol (wt %) | 33.5 |
| propionic acid (wt %) | 1.1 |
| n-propyl aldehyde (wt %) | 1.0 |
| H₂O (wt %) | 13.3 |
| Fuel gas (wt %) | 5.6 |
| Total unidentified Species (wt %) | 1.4 |

EXAMPLE 7

In this example, n-butyl alcohol was reacted with oxygen over Pd on Zeolite Y. As expected, n-butyl butyrate was obtained in good yield with high selectivity.

TABLE 7 n-butyl alcohol conversion catalyzed by Pd on Zeolite Y
Catalyst: Pd on Zeolite Y
Temperature, °C.: 110
WHSV, W/W/Hr.: 0.5
Feed: n-butyl alcohol
Pressure, atm.: 2

| PRODUCT | COMPOSITION |
| --- | --- |
| n-butyl butyrate (wt %) | 24.0 |
| n-butyl alcohol (wt %) | 61.8 |
| butyric acid (wt %) | 0.4 |
| n-butyl aldehyde (wt %) | 2.3 |
| $H_2O$ (wt %) | 7.1 |
| Fuel gas (wt %) | 3.0 |
| Total unidentified Species (wt %) | 1.4 |

Changes and modifications in the specifically described embodiments can be carried out without departing from the scope of the invention, which is intended to be limited only by the scope of the appended claims.

We claim:

1. A process for producing aliphatic esters, R'COOR, from the corresponding alcohol, ROH, where R' and R are alkyl groups with R' having carbon numbers of 1 to 9 and R=R'+1, or when R is a methyl group R' is a hydrogen, consisting essentially of steps:

a. Providing a reactor filled with a dual functional catalyst comprising dispersed metal incorporated by methods including ion exchange and impregnation on zeolitic acid support, b. Introducing a feed containing said alcohol and a predetermined quantity of oxygen to said reactor for substantially vapor phase reaction to form mixtures with composition product K, where K=[R'COOR][$H_2O$]/[ROH][R'COOH], and K is greater than the thermodynamic equilibrium constant of the reaction, and [R'COOR], [$H_2O$], [ROH], and [R'COOH] are concentration of the aliphatic ester, water, alcohol, and aliphatic acid in mole percent, respectively, c. Separating said ester from the reactor effluent, whereby said ester is produced with selectivity greater than 50% and aliphatic acid and gas by-products with selectivity lower than 30%.

2. A process according to claim 1, wherein alcohol content in said feed is substantially less than 95%.

3. A process according to claim 1, wherein by-products are separated and recycled for further reaction.

4. A process according to claim 1, wherein the oxygen is supplied as air.

5. A process according to claim 1, wherein the support for said dual functional catalyst is an acidic porous inorganic material.

6. A process according to claim 1, wherein the Zeolite acidic support for said dual functional catalyst includes Zeolite Y, Zeolite beta, mordenite, and ZSM-5 and their mixtures.

7. A process according to claim 1, wherein the metals on the said dual functional catalyst are selected from the group consisting of noble metals and Group IB, IIB, VIB, VIIB, and VIIIB metals and their combinations.

8. A process according to claim 7, wherein the metal on the said dual functional catalyst includes Pt, Pd, Ru, Rh, Re, Ir and their bimetallic combinations.

9. A process according to claim 7, wherein said metal is in reduced, oxide, or sulfide form.

10. A process according to claim 1, wherein said reaction is conducted substantially in vapor phase by adjusting pressure, temperature, or both.

11. A process according to claim 1, wherein mole ratio of said alcohol to predetermined oxygen supply is about 0.4 to 5, and preferably about 0.6 to 3.

12. A process according to claim 6, wherein silica-alumina ratio of the Zeolite is substantially greater than 5.

13. A process according to claim 1, wherein the conversion level of alcohol, ROH is substantially greater than 20%.

14. A process according to claim 1, wherein the deactivated catalyst from operation of the said process is regenerated in air, oxygen, hydrocarbon, nitrogen, and hot gas from the combustion devices at about 80 C or higher for reuse.

15. A process for production of ethyl acetate from ethanol by oxidation of ethanol, consisting essentially of steps:

a. Providing a reactor filled with a dual functional catalyst comprising metal incorporated by methods including ion exchange and impregnation on zeolitic acid support, b. Introducing a feed containing ethanol and a predetermined quantity of oxygen to said reactor for a vapor phase reaction to form mixtures with composition product K, where K=[EtOAc][$H_2O$]/[EtOH][$CH_3COOH$], and K is greater than the thermodynamic equilibrium constant of 3.7, and [EtOAc], [$H_2O$], [EtOH], and [$CH_3COOH$] are concentration of the ethyl acetate, water, ethanol, and acetic acid in mole percent, respectively, c. Separating ethyl acetate from the reactor effluent, whereby ethyl acetate is produced with selectivity greater than 50% and acetic acid and gas by-products with selectivity lower than 30%.

16. A process according to claim 1, wherein said dual functional catalyst is Pd on Zeolite Y.

* * * * *